United States Patent [19]
Danby

[11] Patent Number: 6,139,531
[45] Date of Patent: Oct. 31, 2000

[54] TUBING RESTORING BUMPERS FOR IMPROVED ACCURACY PERISTALTIC PUMP

[75] Inventor: Hal C. Danby, Nr. Sudbury, United Kingdom

[73] Assignee: Baxter International Inc., Deerfield, Ill.

[21] Appl. No.: 09/034,557

[22] Filed: Mar. 3, 1998

[30] Foreign Application Priority Data

Feb. 5, 1998 [GB] United Kingdom ............... 9802376

[51] Int. Cl.⁷ ........................... A61M 1/00; F04B 43/12
[52] U.S. Cl. ........................................ 604/153; 417/474
[58] Field of Search ........................ 604/153; 417/474

[56] References Cited

U.S. PATENT DOCUMENTS

| | | |
|---|---|---|
| 3,778,195 | 12/1973 | Bamberg . |
| 4,199,307 | 4/1980 | Jassawalla . |
| 4,302,164 | 11/1981 | Manella . |
| 4,893,991 | 1/1990 | Heminway et al. ............ 417/474 X |
| 5,772,409 | 6/1998 | Johnson ....................... 604/153 X |
| 5,823,746 | 10/1998 | Johnson ....................... 417/474 X |

FOREIGN PATENT DOCUMENTS

| | | |
|---|---|---|
| 0411543 A2 | 2/1991 | European Pat. Off. . |
| 0 450 736 | 10/1991 | European Pat. Off. . |
| 0 606 099 | 7/1994 | European Pat. Off. . |
| 0 872 252 | 10/1998 | European Pat. Off. . |
| 2 016 608 | 9/1979 | United Kingdom . |
| WO9605432 | 2/1996 | WIPO . |
| WO9605433 | 2/1996 | WIPO . |
| WO9605434 | 2/1996 | WIPO . |
| WO9605435 | 2/1996 | WIPO . |
| WO9618038 | 6/1996 | WIPO . |

*Primary Examiner*—Jeffrey A. Smith
*Attorney, Agent, or Firm*—Swanson & Bratschun

[57] ABSTRACT

An apparatus in a medical delivery device for biasing tubing having a select original cross-section which is subject to compression and relaxation to substantially its original cross-section upon relaxation. The apparatus includes a plurality of bumpers disposed lengthwise of the tubing operatively associated with the tubing to bias the tubing to its original cross-section and spaced relative to adjacent bumpers to provide for free expansion of the tubing as it is subject to compression.

21 Claims, 3 Drawing Sheets

TUBING RESTORING BUMPERS FOR IMPROVED ACCURACY PERISTALTIC PUMP

BACKGROUND OF THE INVENTION

1. Technical Field

The present invention is directed toward liquid delivery devices for controlling the flow of liquid from a liquid reservoir, and more particularly toward tubing restoring bumpers for an improved accuracy peristaltic pump.

2. Background Art

Peristaltic pumps are particularly suited for use in accurately metering and infusing fluids such as medications into the bodies of hospital patients. Heminway, U.S. Pat. No. 4,893,991, discloses a linear type of peristaltic pump. Natwick, U.S. Pat. No. 5,055,001, discloses a valve/plunger type of peristaltic pump. Galea, U.S. Pat. No. 3,999,891, discloses a rotary type peristaltic pump. Each of these peristaltic pumps operate to propel liquid through a resilient tubing which is typically made from a flexible plastic material such as polyvinyl chloride or the like. The tubing is repeatedly sequentially compressed and expanded along a defined section of the tubing. The tubing is typically expanded or "rebounded" by its internal resiliency. A known problem with this type of pump is that the portions of tubing which are intermittently compressed and expanded tend to fatigue with time. As a result, the tubing is less able to rebound to its original cross-section when released, decreasing the volume of the tubing along the critical pumping segment and thereby degrading pump accuracy. U.S. Pat. No. 4,893,991 notes that such pumps have been found to exhibit as much as a 10% drop in flow rate in a 24 hour period.

The prior art has recognized this short coming in peristaltic pumps and has attempted at least three ways to solve the problem. First, Heminway, U.S. Pat. No. 4,893,991, attempts to improve pump accuracy by preventing the portion of resilient tubing which is subject to compression and expansion from assuming a cylindrical configuration upon expansion. That is, the plungers which compress and expand the tubing are designed to maintain the segment of tubing in an oval cross-section even at full expansion. A principal problem with the solution set forth in Heminway is that it requires very accurate tolerances with the plungers in the retracted position so that the tubing expands to a consistent oval cross-section in order for the pump to operate at accurate rates and volumes. In addition, because the tubing is not able to assume its full circular cross-section, and therefore its greatest volume, Heminway unduly restricts the rate liquid can be pumped.

Natwick, U.S. Pat. No. 5,055,001, proposes an even more complicated solution to improving accuracy in peristaltic pumps. Natwick proposes that the range of diametric compression of the tubing be from about 15% with the plunger retracted to about 85% with the plunger extended. Natwick argues that since the tubing need never recover to a fully uncompressed condition, changes in the elasticity of the flexible tubing due to continued use and repeated compression have much less effect on the volumetric capacity of the pump. In addition, because the plunger never fully compresses the pumping portion of the tubing, the tubing is subjected to less fatigue. Natwick further teaches providing mechanical tubing shapers disposed on each side of the plunger which are extended to reform the pumping portion of the tubing as the plunger is retracted and the tubing refills with fluid. Natwick suffers from the same shortfall of Heminway in that it restricts the volume of the tubing used for pumping and therefore limits pump output rates. In addition, the tubing shapers are complex mechanical structures which create an additional avenue for potential pump failure. Moreover, the mechanical shapers taught in Natwick require a number of potentially costly parts and complicate the assembly of the pump.

Mannes, U.S. Pat. No. 4,585,442, discloses an intravenous infusion rate controller which operates on a resilient tubing which rests in a trough between a pair of resilient bands. The resilient bands act on opposing sides of the outer diameter of the tubing in a compressed state to aid in restoring the tube to its original cross-section upon expansion. In this manner the resilient bands inhibit the tendency of the tube to "flatten out" and rebound to only an oval cross-section which degrades the accuracy of the rate controller. Unfortunately, the resilient bands act on only two discrete points in attempting to restore the tubing to its original shape. Moreover, the space between the resilient bands must be maintained at rather precise tolerances to avoid the resilient bands compressing the tubing into an oval cross-section if the bands are too close or failing to restore the tube to its circular cross-section if the bands are too far apart. In addition, the structure of Mannes requires the resilient bands to be displaced an amount equal to the full displacement of the compressed tubing. As a result, considerable energy must be expended to compress the tubing against the restoring force of the resilient bands.

The present invention is directed toward overcoming one or more of the problems discussed above.

SUMMARY OF THE INVENTION

A first aspect of the present invention is an apparatus in a medical liquid delivery device for biasing a tubing having a select original cross-section which is subject to compression and relaxation to substantially its original cross-section upon relaxation. The apparatus includes a plurality of bumpers disposed lengthwise of tubing and operatively associated with the tubing to bias the tubing to its original cross-section, the bumpers being disposed relative to adjacent lengthwise bumpers to provide for free expansion of the tubing as it is subject to compression. The free expansion of the tubing is preferably provided by lengthwise spacing of adjacent bumpers to define a tubing expansion space therebetween. The plurality of bumpers are further preferably disposed with the bumpers on opposite sides of the tubing. The bumpers on opposite sides of the tubing are spaced from one another a distance substantially equal to an outer diameter equivalent of the original cross-section of the tubing. The compression of the tubing may be provided by a plunger acting on a select lengthwise segment of the tubing, the plunger having a compression surface corresponding to the lengthwise segment of the tubing. The tubing expansion space is adjacent the lengthwise segment of the tubing. The bumpers are preferably made of an elastomer.

Another aspect of the invention is a peristaltic pump for delivering liquid from a liquid reservoir to a select location. The peristaltic pump includes a resilient tubing having a wall defining a flow lumen, with the flow lumen being in liquid communication with the reservoir. A plurality of bumpers are disposed lengthwise of a pumping segment of the tubing. Each bumper of each bumper pair is disposed on an opposite side of the tubing as the other bumper and spaced a distance substantially equal to an equivalent outer diameter of the tubing. Each adjacent bumper pair is spaced a distance lengthwise of the pumping segment of the tubing to define a tubing expansion space. A plunger corresponds to each tubing expansion space and is operatively associated with the pumping segment of the tubing. Each plunger is selectively extended and retracted relative to a lengthwise segment of the pumping segment between an extended and retracted position, with the plunger in the extended position collapsing the flow lumen into a collapsed state and the plunger in the retracted position enabling the tubing wall to be restored to an uncollapsed state. A drive sequentially moves the plungers between the extended and retracted positions so as to move liquid through the flow lumen from the reservoir to the select location. Preferably, the bumpers are made of an elastomer. The peristaltic pump may further include a trough defined between opposing walls of a support block sized to receive the pumping segment of the tubing. The bumpers are disposed between the opposing walls of the support block and the wall of the resilient tubing. The support block and the bumpers are preferably integrally formed of a single piece of an elastomer.

Another aspect of the present invention is a liquid delivery device for controlling the flow of liquid from a liquid reservoir. The liquid delivery device includes a resilient tubing having a wall defining a flow lumen, the flow lumen being in liquid communication with the reservoir. Two bumper pairs are disposed lengthwise of a control segment of the tubing. Each bumper of each bumper pair is disposed on an opposite side of the tubing as the other bumper and spaced a distance substantially equal to an equivalent outer diameter of the tube. The bumper pairs are spaced a distance lengthwise of the control segment of the tubing to define a tubing expansion space. A plunger corresponding to the tubing expansion space is operatively associated with the control segment of the tubing. The plunger is selectively extended and retracted relative to a lengthwise segment of the control segment of the tubing between an extended position and a retracted position, with the plunger in the extended position collapsing the flow lumen into a collapsed state and the plunger in the retracted position enabling the flow lumen to be restored to an uncollapsed state. In this manner, the effective cross-sectional area of the flow lumen is varied to vary the liquid flow capacity of the flow lumen. Preferably, the liquid delivery device further includes a support block have a trough sized to receive the pumping segment of the tubing. The trough is defined between opposing walls of the support block and the bumpers are disposed between the opposing walls of the support block and the resilient tubing. The support block and the bumpers are preferably integrally formed of a single piece of an elastomer.

The plurality of bumpers operatively disposed relative to the pumping segment of a tubing bias the pumping segment of the tubing to its cylindrical configuration. Expansion spaces corresponding to the plungers receive a portion of the displaced tubing wall, negating the need to displace the bumpers themselves. In this manner the amount of energy required to collapse the tube is reduced from the amount of energy that would be required to compress the tubing were the distorted portion of the tubing required to displace the bumpers. The close lengthwise spacing of the bumpers enable the bumpers to help fully restore the tubing to its original uncompressed cross-sectional configuration when the plunger is moved to an unextended position. Thus, improved accuracy of the peristaltic pump is provided by biasing the tubing to its uncompressed configuration when the plunger is in its unextended position, while a minimum amount of energy is required to compress the tubing as the plunger is extended. The minimization of energy consumption can be of enormous significance, particularly where the peristaltic pump is used with ambulatory patients and is driven by batteries. The decreased power requirements can significantly extend the life of the batteries. Furthermore, because less energy is required to compress the tubing a smaller drive motor can be employed, further diminishing energy requirements and allowing for manufacture of more efficient, smaller sized and lighter weight peristaltic pumps.

DETAILED DESCRIPTION OF THE PREFERRED EMBODIMENT

Figure 1:
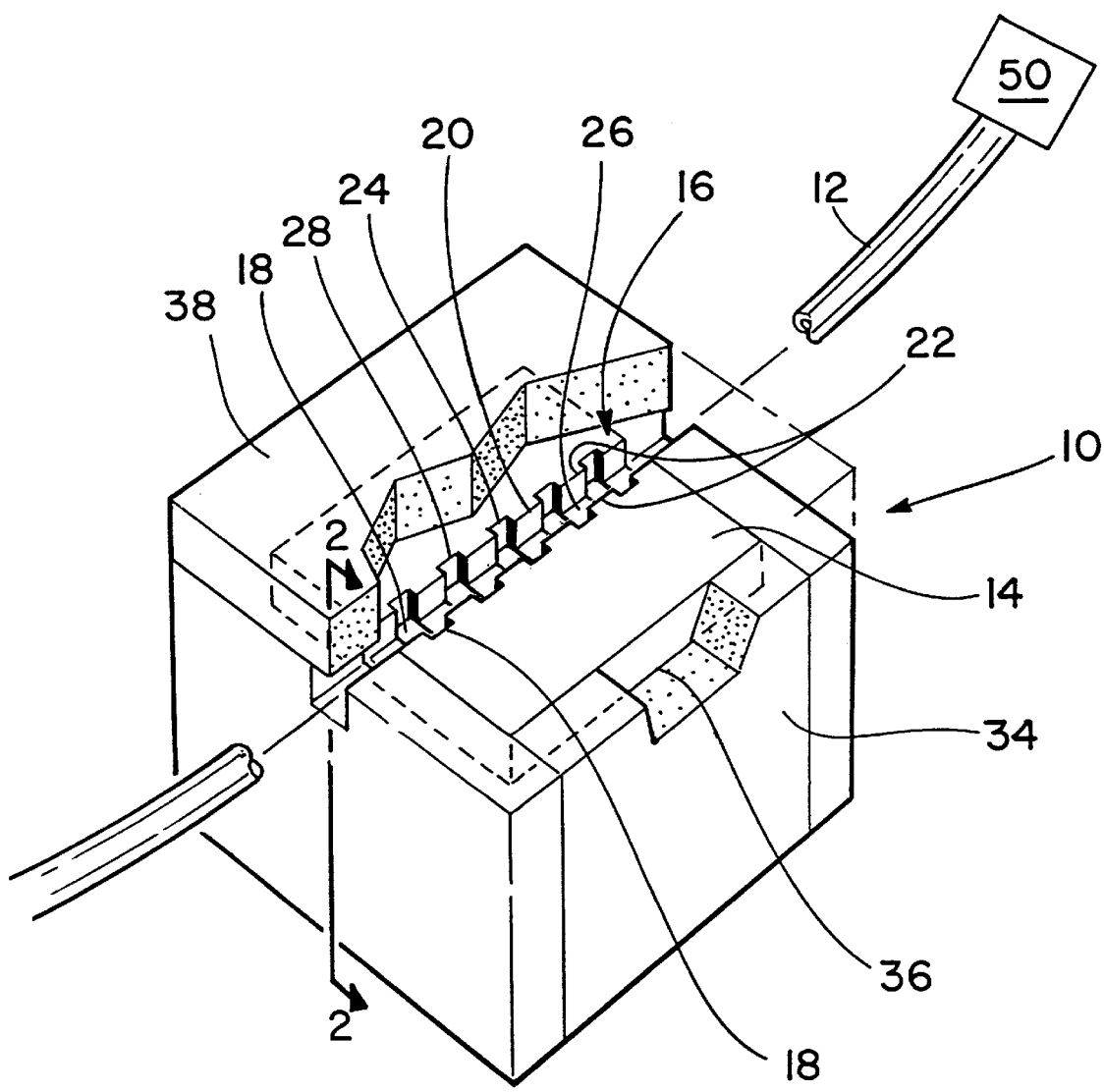
FIG. 1 is a perspective view of a pumping mechanism of a peristaltic pump in accordance with the present invention with a portion of the platen and the pump drive removed for clarity.

The pumping mechanism 10 of an improved accuracy peristaltic pump is shown in a perspective view in FIG. 1. The pumping mechanism includes a resilient cylindrical tubing 12. The cylindrical tubing 12 is made from a flexible plastic material such as polyvinyl chloride and is well known in the art. A support block 14 has a trough 16 formed therein defined between opposing walls 18. A number of bumpers 20 extend into the trough from the opposing walls 18. The bumpers 20 are disposed in bumper pairs 22 extending toward one another from the opposing walls 18. Each bumper 20 of each bumper pair 22 is spaced from the other a distance substantially equal to the outer diameter of the cylindrical tubing 12, which is received there between. The bumper pairs 22 are spaced lengthwise along the trough 16 to define expansion spaces 24 for free expansion of the tubing when it is subject to compression. Bridges 26 extend between bumpers pairs 22. Between adjacent bridges is defined a path 28. As better seen in FIG. 3, the path 28 receives a plunger 32. In the embodiment illustrated in FIG. 1, the support block 14, bumpers 20 and bridges 26 are integrally formed from a single block of an elastomer. Alternatively, the bumpers 20 could be formed of an elastomer while the support 14 is made of a rigid material, such as a metal or rigid thermoplastic. Furthermore, the bridge 26 could be eliminated without preventing the bumpers from performing their intended function as discussed further below.

The pumping mechanism 10 further includes a housing 34 including a cavity 36 configured to receive the support block 14. The housing 34 is preferably made of a rigid material such as a metal to confine the support block 14. A platen 38 fits across the mouth of the trough 16 to provide a surface against which the tubing 12 is collapsed by the plungers 32, as illustrated and described below with regard to FIG. 2. Although not illustrated, the platen is preferably part of a door which can be pivoted open to permit access to the trough for loading the tube 12 into the trough.

Figure 2:
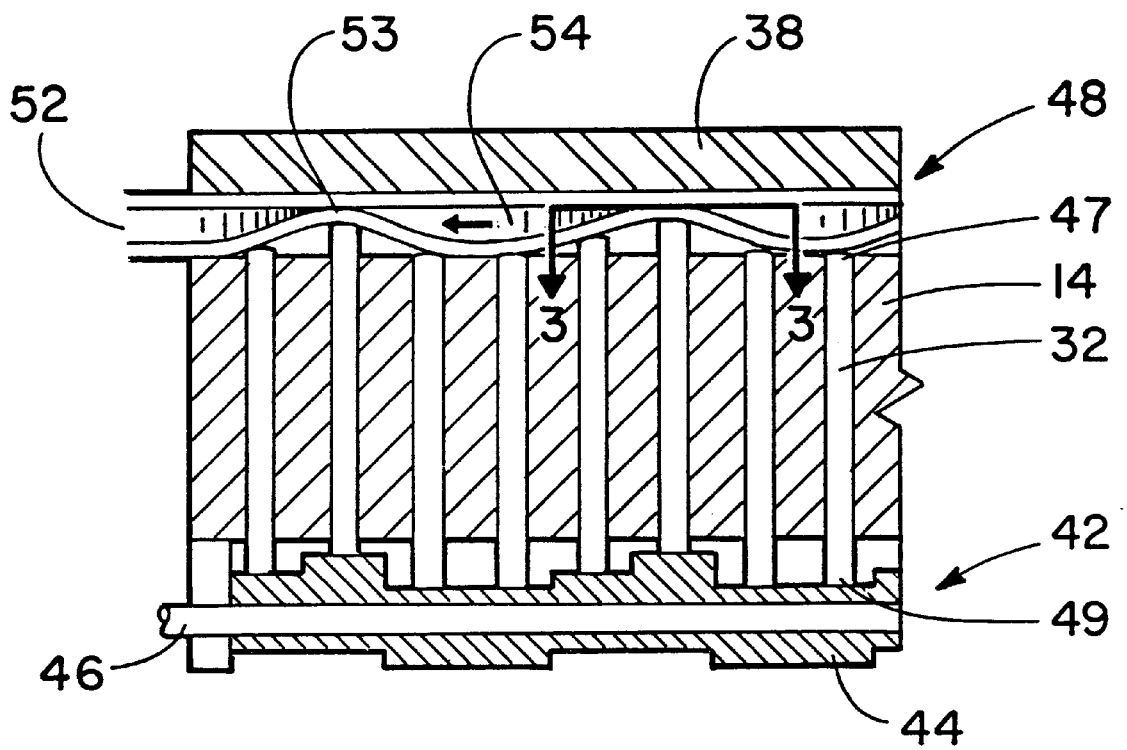
FIG. 2 is a sectional, elevational view taken along line 2—2 of FIG. 1.

The pumping mechanism 10 further includes a pump drive 42, shown in FIG. 2. The pump drive 42 consists of a number of cams 44 eccentrically connected to a drive shaft 46. The drive shaft 46 is in turn operatively associated with drive motor, which is not shown. The plungers 32 have one end 47 operatively associated with a pumping segment 48 of the tubing defining a compression surface and a second end 49 associated with a cam 44. As is well known in the art, the pump drive 42 is configured to sequentially extend and retract the plungers 32 relative to a lengthwise segment of the pumping segment of the tube between an extended position to pump liquid from the reservoir 50 and a retracted position. With the plunger in the extended position, the flow lumen 52 of the tube 12 is collapsed to a collapsed state 53 and with the plunger in the retracted position a flow lumen is restored to an uncollapsed state 54.

Figure 3:
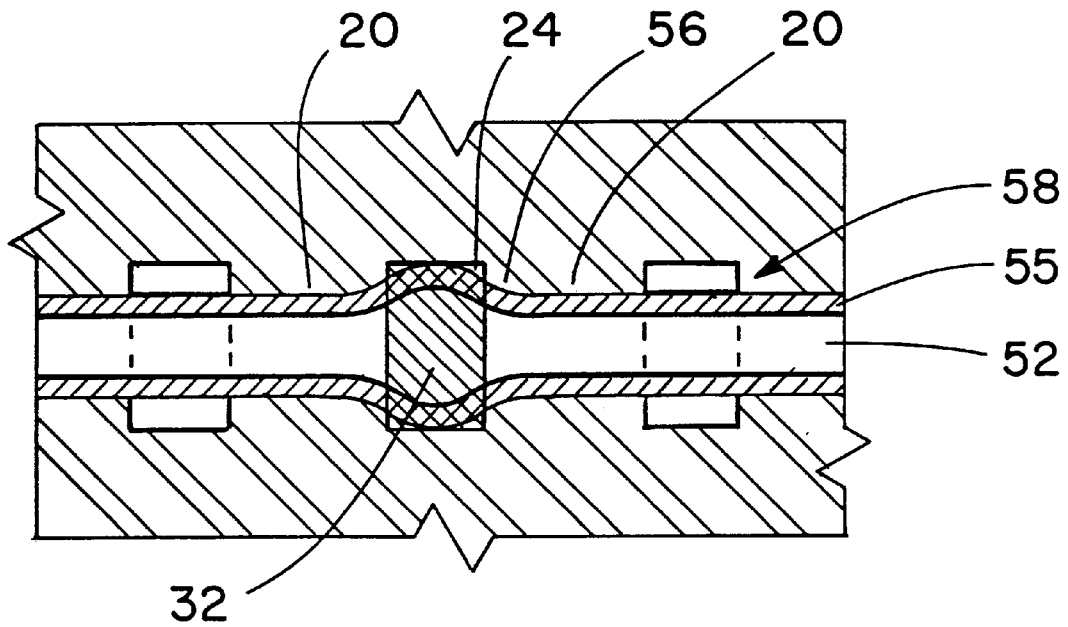
FIG. 3 is a sectional plan view taken along line 3—3 of FIG. 2.

FIG. 3 illustrates the function of the bumpers 20. With the plunger 32 in the extended position, a lengthwise segment of the pumping portion of the tubing wall 55 is expanded or deformed and pushed into the expansion space 24 between adjacent bumpers 20. When this occurs, the corners 56 of the bumpers 20 are compressed as illustrated in FIG. 3, as is a contiguous portion of the support block 14. When the plunger returns to its retracted position, the compressed elastomeric bumpers and contiguous portion of the support block 14 function along with the resilient wall of the tubing to restore the tubing to its original configuration, as seen at 58. A principal advantage of the expansion space 24 is that the deformed portion of the tubing wall 55 fills this expansion space without having to deform a corresponding section of the bumper 20. In this manner, the energy required to compress the tube wall 55 is minimized. However, the bumpers are close enough to provide substantial assistance in restoring the tubing to its original cross-section. As illustrated in FIG. 3, the compression surface of the plunger 32 preferably substantially fills the cross-section of the expansion space 24.

Figure 4:
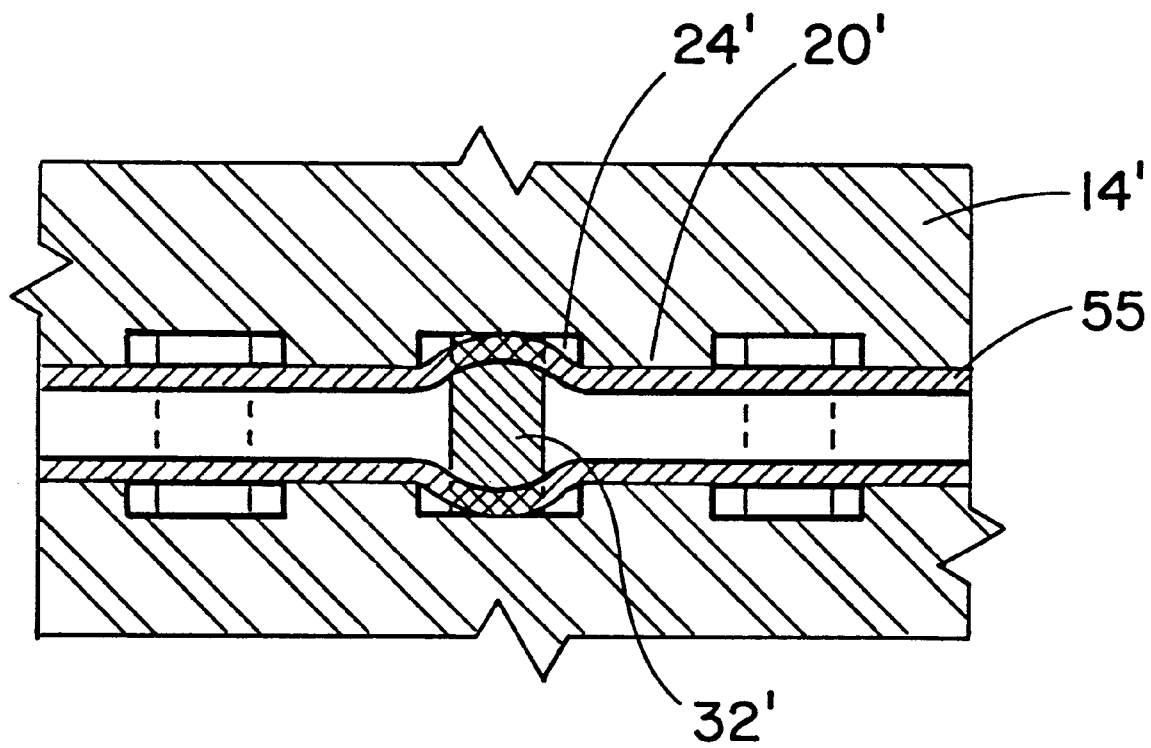
FIG. 4 is an alternate embodiment of the invention from the same perspective as FIG. 3.

FIG. 4 illustrates an alternate embodiment of the invention. In this embodiment, the bumpers 20' and the support block 14' are formed of the rigid material. In order to provide a suitable volume for the tubing wall 55 when it is deformed, the expansion spaces 24' are wider than the plunger 32'. Still, the relative close proximity of the bumpers 20' helps to restore the tubing to its original cross-section when the plunger 32' returns to its retracted position.

The improved pumping mechanism of the peristaltic pump of the present invention provides assistance to the resilient tubing in restoring itself to its original cross-section following compression by a plunger, while minimizing the energy required for the plunger to collapse the flow lumen. By minimizing the amount of energy necessary to collapse the tubing, smaller power supplies can be utilized and smaller, lighter weight motors can be used to drive the pump. Moreover, smaller, lighter weight drive mechanisms can be used, all contributing to smaller, lighter, more efficient peristaltic pumps.

What is claimed is:

1. A medical liquid delivery device subjecting a tubing segment of a tubing having a select original cross-section to compression and relaxation, wherein the improvement comprises:

a plurality of elastomeric bumpers disposed lengthwise of the tubing operatively associated with the tubing to bias the tubing segment to substantially its original cross-section, the bumpers being disposed relative to adjacent lengthwise bumpers to provide for free expansion of the tubing segment as it is subject to compression.

2. The medical delivery device of claim 1, the improvement further comprising the free expansion of the tubing segment being provided by lengthwise spacing of adjacent bumpers to define a tubing expansion space therebetween.

3. The medical delivery device of claim 2, the improvement further comprising the tubing segment being subject to compression by a plunger having a compression surface corresponding to the tubing segment, the tubing expansion space being adjacent the tubing segment.

4. The medical delivery device of claim 3, the improvement further comprising the compression surface of the plunger substantially filling a cross-section of the tubing expansion space.

5. The medical delivery device of claim 1, the improvement further comprising the plurality of bumpers being further disposed with bumpers on opposite sides of the tubing spaced from one another a distance substantially equal to an outer diameter equivalent of the original cross-section of the tubing.

6. The medical delivery device of claim 1, the improvement further comprising the bumpers being disposed in bumper pairs lengthwise of the tubing, each bumper of each bumper pair being disposed on an opposite side of the tubing and spaced a distance substantially equal to an outer diameter equivalent of the original cross-section of the tubing.

7. The medical delivery device of claim 6, the improvement further comprising the free expansion of the tubing being provided by lengthwise spacing of adjacent bumpers to define a tubing expansion space therebetween.

8. The medical delivery device of claim 1, the improvement further comprising a support block having a trough therein sized to receive the tubing lengthwise, the trough being defined between opposing walls of the support block and the bumpers being disposed between the opposing walls of the support block and the tubing.

9. The medical delivery device of claim 8, the improvement further comprising the bumpers and the support block being integrally formed from a single piece of an elastomer.

10. A peristaltic pump for delivering liquid from a liquid reservoir to a select location, the peristaltic pump comprising:

a resilient tubing having a wall defining a flow lumen, the flow lumen being in liquid communication with a reservoir;

a plurality of plungers each operatively associated with and spaced lengthwise of a pumping segment of the tubing, each plunger being selectively extended and retracted relative to a lengthwise segment of the pumping segment between an extended position and a retracted position, with the plunger in the extended position collapsing the flow lumen of the lengthwise tubing segment into a collapsed state and the plunger in the retracted position enabling the flow lumen of the lengthwise tubing segment to be restored to an uncollapsed state;

a plurality of bumper pairs disposed lengthwise of the pumping segment of the tubing, each bumper of each bumper pair being disposed on an opposite side of the tubing as the other bumper and spaced a distance substantially equal to an equivalent outer diameter of the tube, each adjacent bumper pair being spaced a distance lengthwise of the pumping segment of the tubing to define a distinct tubing expansion space therebetween corresponding to each plunger; and a drive sequentially moving the plungers between the extended and retracted positions so as to move the liquid through the flow lumen from the reservoir to the select location.

11. The peristaltic pump of claim 10 wherein the bumpers are made of an elastomer.

12. The peristaltic pump of claim 10 wherein the plunger is configured to substantially fill the expansion space.

13. The peristaltic pump of claim 10 further comprising a support block having a trough therein sized to receive the pumping segment of the tubing, the trough being defined between opposing walls of the support block, the bumpers being disposed between the opposing walls of the support block and the wall of the resilient tubing.

14. The peristaltic pump of claim 13 wherein the support block is made of an elastomer.

15. The peristaltic pump of claim 13 wherein the support block and the bumpers are integrally formed from a single piece of an elastomer.

16. The peristaltic pump of claim 15 further comprising a bridge integrally formed with the bumpers and support block extending between each bumper of each bumper pair, with adjacent bridges defining therebetween a path for the plunger into the trough.

17. A liquid delivery device for controlling the flow of liquid from a liquid reservoir, the liquid delivery device comprising:

a resilient tubing having a wall defining a flow lumen, the flow lumen being in liquid communication with a reservoir;

two pairs of elastomeric bumpers disposed lengthwise of a control segment of the tubing, each bumper of each bumper pair being disposed on an opposite side of the tubing as the other bumper and spaced a distance substantially equal to an equivalent outer diameter of the tube, the bumper pairs being spaced a distance lengthwise of the control segment of the tubing to define therebetween a tubing expansion space;

a plunger corresponding to the tubing expansion space is operatively associated with the control segment of the tubing, the plunger being selectively extended and retracted relative to a lengthwise segment of the control segment between an extended position and a retracted position, with the plunger in the extended position collapsing the flow lumen into a collapsed state and the plunger in the retracted position enabling the flow lumen to be restored to an uncollapsed state, whereby the effective cross-sectional area of the flow lumen can be varied to vary the flow capacity of the flow lumen.

18. A peristaltic pump for delivering liquid from a liquid reservoir to a select location, the peristaltic pump comprising:

a resilient cylindrical tubing having a wall defining a flow lumen, the flow lumen being in liquid communication with a reservoir;

a support block having a trough therein receiving a pumping segment of the tubing, the trough being defined between opposing walls of the support block, the support block further comprising a plurality of elastomeric bumper pairs extending into the trough from the opposing walls and disposed lengthwise of the pumping segment of the tubing, each bumper of each bumper pair being disposed on an opposite side of the tubing as the other bumper and spaced a distance substantially equal to the outer diameter of the tubing to bias the tubing into its cylindrical configuration, each adjacent bumper pair being spaced a distance lengthwise of the pumping segment of the tubing to define therebetween a tubing expansion space;

a plunger corresponding to each tubing expansion space operatively associated with the pumping segment of the tubing, each plunger being selectively extended and retracted relative to a lengthwise segment of the pumping segment between an extended position and a retracted position, with the plunger in the extended position collapsing the flow lumen into a collapsed state and the plunger in the retracted position enabling the tubing wall and adjacent bumpers to restore the flow lumen to an uncollapsed state; and a drive sequentially moving the plungers between the extended and retracted positions so as to move the liquid through the flow lumen from the reservoir to the select location.

19. The peristaltic pump of claim 18 wherein the plunger is configured to substantially fill the expansion space.

20. The peristaltic pump of claim 18 wherein the support block and the bumpers are integrally formed from a single piece of an elastomer.

21. The peristaltic pump of claim 18 further comprising a bridge integrally formed with the bumpers and support block extending between each bumper of each bumper pair, with adjacent bridges defining therebetween a path for the plunger into the trough.

* * * * *